United States Patent [19]

Dewey et al.

[11] 4,388,240
[45] Jun. 14, 1983

[54] 6-CHLORO-7,8-DIHYDROXY-1-(p-HYDROXYPHENYL)-2,3,4,5-TETRAHYDRO-1H-3-BENZAZEPINE SULFATE ESTERS

[75] Inventors: Richard H. Dewey, Philadelphia; Bruce Y. Hwang, Broomall, both of Pa.; George Y. Kuo, Cherry Hill, N.J.

[73] Assignee: SmithKline Beckman Corporation, Philadelphia, Pa.

[21] Appl. No.: 337,227

[22] Filed: Jan. 6, 1982

[51] Int. Cl.³ ............... A61K 31/55; C07D 223/16
[52] U.S. Cl. ......................... 260/239 BB; 424/244
[58] Field of Search ............................ 260/239 BB

[56] References Cited

U.S. PATENT DOCUMENTS 4,197,297  4/1980  Weinstock ............... 260/239 BB X

Primary Examiner—Nicholas S. Rizzo
Assistant Examiner—D. B. Springer
Attorney, Agent, or Firm—William H. Edgerton; Richard D. Foggio; Alan D. Lourie

[57] ABSTRACT

New 6-chloro-7,8-dihydroxy-1-(p-hydroxyphenyl)-2,3,4,5-tetrahydro-1H-3-benzazepine hydrogen sulfate monoesters have been prepared and found to have potent renal dopaminergic activity. The most potent compound of the series is 6-chloro-7,8-dihydroxy-1-phenyl-2,3,4,5-tetrahydro-1H-3-benzazepin-4'-yl-hydrogen sulfate.

3 Claims, No Drawings

6-CHLORO-7,8-DIHYDROXY-1-(p-HYDROXY-PHENYL)-2,3,4,5-TETRAHYDRO-1H-3-BENZAZEPINE SULFATE ESTERS

This invention concerns a new group of chemical compounds which are 6-chloro-7,8-dihydroxy-1-(p-hydroxyphenyl)-2,3,4,5-tetrahydro-1H-3-benzazepine mono-hydrogen sulfate esters. The compounds have renal dopaminergic activity and, thereby, utility for treating hypertension or improving renal function in patients in need of such treatment. They are also metabolic products formed in vivo after administration of the parent compound or one of its salts either orally or parenterally.

STATEMENT OF THE PRIOR ART

U.S. Pat. No. 4,197,297 describes 6-chloro-7,8-dihydroxy-1-(p-hydroxyphenyl)-2,3,4,5-tetrahydro-1H-3-benzazepine and its unique peripheral dopamine agonist activity. The generic class of sulfate esters of this compound is mentined in EPO patent application No. 22,330 published Jan. 14, 1981 as possible alternative ingredients for preparing a dosage unit containing, in combination, a renal dopaminergic compound and a diuretic agent. The information in the EPO application was derived from the present applicants. The EPO application is directed to a different invention than the one described and claimed hereafter.

DESCRIPTION OF THE INVENTION

The compounds of this invention are represented by the following structural formula:

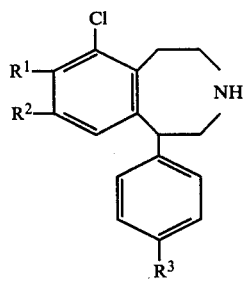

in which one of $R^1$, $R^2$ or $R^3$ is hydrogen sulfato (—OSO$_3$H) and the other two are hydroxy.

The compounds of Formula I in which the hydrogen sulfato group is at the 7 or 8-position were first isolated as urinary metabolites of 6-chloro-7,8-dihydroxy-1-(p-hydroxyphenyl)-2,3,4,5-tetrahydro-1H-3-benzazepine methanesulfonate in rats and particularly in dogs. In the latter species the 7 or 8-sulfate esters comprise 50% of the urinary metabolites in about equal parts. The compounds were separated from the urine of the treated animals using chromatographic separation over a hydrophobic polystyrene resin column (Amberlite XAD-2) followed by high pressure liquid chromatography as described hereafter.

Following this discovery, the three sulfate esters of this invention were prepared by sulfation of 6-chloro-7,8-dihydroxy-1-(p-hydroxyphenyl)-2,3,4,5-tetrahydro-1H-3-benzazepine with a slight excess of one molar equivalent of chlorosulfonic acid in pyridine-dimethylformamide. During isolation of the three specific esters from the reaction mixture, the 4'-hydrogen sulfate (Formula I, $R^1$ and $R^2$ are —OH, $R^3$ is —OSO$_3$H) is most easily separated. The 7- and 8-isomers are difficult to separate because of their low solubility and other similar physical characteristics.

Surprisingly, the compounds have been found to be potent renal dopaminergic agents in their own right in the anesthetized dog protocol described in U.S. Pat. No. 4,197,297. In this test the 4'-isomer was more potent than the other isomers.

The renal biological activity of the compounds of this invention is unexpected since sulfate esters are known in the art often not to be altered in the mammalian body by metabolism after absorption since they are already in conjugated form suitable for excretion. Also the O-glucuronide which is another metabolic product of the present parent compound isolated, particularly in the rat, has poor dopaminergic activity.

The following example demonstrates the preparation of the new compounds of this invention as well as their renal activity.

EXAMPLE 1

To a mixture of 1.6 g (0.02 m) of dry pyridine and 10 ml of dry dimethylformamide was added dropwise 0.88 g (0.0075 m) of chlorosulfonic acid with ice-cooling (caution: this reaction produces considerable amount of heat and fumes). This pyridine —SO$_3$ complex solution was then added to a solution of 2.0 g (0.005 m) of 6-chloro-7,8-dihydroxy-1-(p-hydroxyphenyl)-2,3,4,5-tetrahydro-1H-3-benzazepine methane sulfonate in 100 ml of dry pyridine. The mixture was heated at 60°-70° C. for 1 hour, then cooled and mixed with 600 ml of ether to precipitate a gummy residue which is a mixture of the three isomeric sulfate esters.

The gummy product mixture was purified in a Waters Associates prep LC 500 high pressure liquid chromatographic apparatus using a Partisil 10 ODS-2 reverse phase column with 0.05 M ammonium acetate buffer, pH of 4, 10 methanol/90 buffer as the mobile phase with a flow rate of 250 ml/min using a differential refractometer as a detector. Early cut fractions gave 200 mg of white crystals of 6-chloro-7,8-dihydroxy-1-phenyl-2,3,4,5-tetrahydro-1H-3-benzazepin-4'-yl-hydrogen sulfate, m.p. 172°-175° C. upon standing overnight.

Anal. Calcd. for C$_{16}$H$_{16}$ClNO$_6$S.2½H$_2$O: C, 44.60; H, 4.90; N, 3.25. Found: C, 44.75; H, 4.86; N, 3.18.

This compound in the anesthetized dog protocol for dopaminergic activity (2 dogs) gave the following data:

| Drug | Dose μg/kg/min | % change from control | | | |
|---|---|---|---|---|---|
| | | MAP | RBF | RVR | HR |
| Dopamine | 3 | −5.9 | +17.8 | −20.0 | 0 |
| 4'-sulfate | 3 | −6.9 | +18.3 | −21.4 | 0 |
| | 30 | −12.0 | +22.6 | −27.7 | +4.8 |

MAP is mean arterial pressure; RBF is renal blood flow; RVR is renal vascular resistance; HR is heart rate.

These data indicate the sulfate ester is slightly less active than is the parent compound. Medical dosage units and methods of use employing the compounds of this invention as active ingredients are similar to those of U.S. Pat. No. 4,197,297 column 6 line 19 to column 7 line 48.

The remaining fractions from the column were combined and concentrated under aspirator pressure at 30°. The residue was again put through the high pressure liquid chromatographic procedure as described above with 10 cuts made. Fraction 4 contained additional 4′-sulfate. Fractions 8, 9 and 10 gave 120 mg of a mixture of 7 and 8-isomers in a 1:6 ratio, m.p. 262°–265° C.

Anal. Calcd. for $C_{16}H_{16}ClNO_6S\cdot 1H_2O$: C, 47.59; H, 4.49; N, 3.47; S, 7.94. Found: C, 47.67; H, 4.53; N, 3.38; S, 7.68.

A sample of the 7,8-isomeric mixture was treated with 3 N hydrochloric acid to give the parent base.

The 8-hydrogen sulfate gave the following data in 2 anesthetized dogs.

| Drug | Dose μg/kg/min | % change from control | | | |
|---|---|---|---|---|---|
| | | MAP | RBF | RVR | HR |
| Dopamine | 3 | −5.5 | +21.0 | −21.5 | +10.5 |
| 8-sulfate* | 3 | −2.0 | +11.0 | −11.5 | 0 |
| | 30 | −9.0 | +14.5 | −20.5 | +10.0 |
| | 300 | −9.5 | −4.0 | −4.5 | 0 |

*Contains over 85% 8-isomer with less than 15% 7-isomer.

The structure of the three hydrogen sulfate esters was confirmed by the following nuclear magnetic resonance data (NMR carbon 13) obtained on a Varian FT-80 machine. Numbering is to the classical positions of the skeletal structure:

| Carbon | Parent | 4′ | 7 | 8 |
|---|---|---|---|---|
| 6 | 120.76 | 120.81 | 127.63 | 121.67 |
| 7 | 140.22 | 140.50 | 141.00 | 139.50 |
| 8 | 144.01 | 144.21 | 149.02 | 144.80 |
| 9 | 114.34 | 114.25 | 116.86 | 122.16 |
| 6a (bridge) | 126.23 | 126.19 | 128.82 | 132.88 |
| 9a (bridge) | 134.11 | 134.84 | 141.00 | 134.23 |
| 1′ | 130.71 | 133.46 | 130.28 | 130.27 |
| 2′ | 129.16 | 128.57 | 129.28 | 129.19 |
| 3′ | 115.67 | 120.63 | 115.81 | 115.80 |
| 4′ | 156.23 | 152.54 | 156.53 | 156.44 |

The H-nuclear magnetic resonance analysis on a Perkin-Elmer R32 apparatus gave the following chemical shifts and coupling constants.

| Compound | $C_9$-Proton | 2′ and 3′ Protons |
|---|---|---|
| parent | 6.1 | 6.8 and 7.0 J = 6Hz |
| 7 | 6.1 | 6.8 and 7.0 J = 6Hz |
| 8 | 6.4 | 6.8 and 7.0 J = 6Hz |
| 4′ | 6.1 | 7.05 and 7.25 J = 8Hz |

What is claimed is:
1. 6-Chloro-7,8-dihydroxy-1-phenyl-2,3,4,5-tetrahydro-1H-3-benzazepin-4′-yl-hydrogen sulfate.
2. 6-Chloro-7-hydroxy-1-(p-hydroxyphenyl)-2,3,4,5-tetrahydro-1H-3-benzazepin-8-yl-hydrogen sulfate being substantially free from its 7-isomer.
3. 6-Chloro-8-hydroxy-1-(p-hydroxyphenyl)-2,3,4,5-tetrahydro-1H-3-benzazepin-7-yl-hydrogen sulfate being substantially free from its 8-isomer.

* * * * *